United States Patent
Lavender et al.

(10) Patent No.: US 11,458,075 B2
(45) Date of Patent: Oct. 4, 2022

(54) ORAL CARE COMPOSITION HAVING ENHANCED APPEARANCE AND FORM

(71) Applicant: Colgate-Palmolive Company, New York, NY (US)

(72) Inventors: Stacey Lavender, Chesterfield, NJ (US); Najma Khan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 16/342,596

(22) PCT Filed: Oct. 17, 2016

(86) PCT No.: PCT/US2016/057362
§ 371 (c)(1),
(2) Date: Apr. 17, 2019

(87) PCT Pub. No.: WO2018/075001
PCT Pub. Date: Apr. 26, 2018

(65) Prior Publication Data
US 2019/0254935 A1     Aug. 22, 2019

(51) Int. Cl.
*A61K 6/70* (2020.01)
*A61Q 11/00* (2006.01)
*A61K 8/73* (2006.01)
*A61K 8/21* (2006.01)
*A61K 8/92* (2006.01)

(52) U.S. Cl.
CPC ............. *A61K 6/70* (2020.01); *A61K 8/21* (2013.01); *A61K 8/73* (2013.01); *A61K 8/922* (2013.01); *A61Q 11/00* (2013.01)

(58) Field of Classification Search
CPC combination set(s) only.
See application file for complete search history.

(56) References Cited

U.S. PATENT DOCUMENTS

| | | | |
|---|---|---|---|
| 5,240,710 A * | 8/1993 | Bar-Shalom | A61K 8/73 424/422 |
| 5,380,530 A | 1/1995 | Hill | |
| 8,568,697 B2 * | 10/2013 | Joziak | A61K 8/21 424/49 |
| 9,561,160 B2 | 2/2017 | Rege et al. | |
| 9,689,595 B2 * | 6/2017 | Zhan | F16K 3/265 |
| 10,064,881 B2 * | 9/2018 | Silberstein | A61K 8/737 |
| 2004/0136924 A1 * | 7/2004 | Boyd | A61K 8/731 424/48 |
| 2009/0053267 A1 | 2/2009 | Depierro et al. | |
| 2016/0000667 A1 | 1/2016 | Potnis et al. | |
| 2016/0068579 A1 | 3/2016 | Gemperli et al. | |
| 2017/0354577 A1 | 12/2017 | Lavender et al. | |

FOREIGN PATENT DOCUMENTS

| | | | |
|---|---|---|---|
| CN | 105596260 | * | 5/2016 |
| CN | 105596260 A | * | 5/2016 |
| DE | 551888 C | | 6/1932 |
| RU | 2280437 | | 7/2006 |
| WO | 2010/054829 | | 5/2010 |
| WO | 2013/030635 | | 3/2013 |

OTHER PUBLICATIONS

Raj A, A review on pectin, Open access scientific reports, 1(12), 2012, 1-4 (Year: 2012).*
purefiji.com (https://www.purefiji.com/blog/benefits-coconut-oil/#:-:text=Not%20only%20is%20coconut%20oil,amazing%20moisturizer%20for%20your%20body.&text=Coconut%20oil%20can%20help%20to,lotions%2C%20creams%20and%20body%20butters. Mar. 21, 2016) (Year: 2016).*
Endress, 1991, "Chapter 12: Nonfood Uses of Pectin," The Chemistry and Technology of Pectin, pp. 251-268.
International Search Report and Written Opinion of the International Searching Authority in International Application No. PCT/US2016/057362, dated Dec. 21, 2016.

* cited by examiner

*Primary Examiner* — Celeste A Roney

(57) ABSTRACT

Provided is an oral care composition and methods of making and using the same. The composition may include an orally acceptable vehicle, including pectin in an amount of from about 0.1% to about 1% by weight, an anticaries agent; and a moisturizing agent.

9 Claims, No Drawings

ORAL CARE COMPOSITION HAVING ENHANCED APPEARANCE AND FORM

CROSS REFERENCE TO RELATED APPLICATIONS

This application is National Stage Entry under 35 U.S.C. § 371 claiming the benefit and priority of PCT/US2016/057362, filed Oct. 17, 2016.

BACKGROUND

An effective oral care composition should provide maintenance and preservation of tooth appearance through cleaning of teeth and gums, removal of dental stains, and the polishing of the teeth. It should clean and remove exogenous debris, thereby aiding the prevention of tooth decay and promoting gingival health as well as providing clean and fresh mouth feel. However, conventional dentifrice compositions tend to be drying due to silicas and/or surfactants. This effect can exacerbate the symptoms of xerostomia, or "dry mouth", in which a person experiences or perceives a deficient amount of saliva in the mouth, leading to insufficient mucosal wetting, especially of the oral palate.

As a result, it is desirable for a dentifrice composition to provide clean mouth feel and freshened breath while ameliorating the perception of dry mouth, such as that associated with xerostomia, and to provide positive mouth and/or tooth feel benefits. To provide relief from the symptoms of dry mouth, moisturizing agents such as oils are added to oral care formulations in order to lower the coefficient of friction. However, the addition of oil can lower the viscosity of the oral care formulation. Thus, in the case of a toothpaste, lower viscosity results in "sinking" between the bristles of a toothbrush. From a consumer viewpoint, toothpaste that sinks into the bristles may be perceived as too thin or watery. Therefore, it is desirable to form an oil-containing oral care composition with enhanced product appearance and form that addresses these shortcomings.

BRIEF SUMMARY

In an embodiment, an oral care composition comprises: an orally acceptable vehicle comprising pectin in an amount of from about 0.1% to about 1% by weight, an anticaries agent; and a moisturizing agent. 2.

In an implementation of the oral care composition, the moisturizing agent comprises coconut oil. In an example, the coconut oil is present in an amount greater than about 0.01% to less than about 5% by weight. In an example, the coconut oil is present in an amount of about 2.5% by weight.

In an implementation of the oral care composition, the oral care composition exhibits a viscosity greater than about 400,000 centipoise.

In an implementation of the oral care composition, the oral care composition exhibits a viscosity greater than about 500,000 centipoise.

In an implementation, the oral care composition, further comprises at least one abrasive.

In an implementation of the oral care composition, the abrasive agent is selected from the group consisting of silica, alumina, insoluble phosphate, calcium carbonate, resinous abrasive, and mixtures thereof.

In an implementation, the oral care composition further comprises at least one humectant, and at least one surfactant.

In an implementation, the oral care composition further comprises one or more agents selected from abrasives, diluents, pH modifying agents, surfactants, foam modulators, thickening agents, humectants, sweeteners, flavorant, anticalculus or tartar control agents, and mixtures thereof. In an example, the anticaries agent comprises a fluoride ion source. In an example, the anticaries agent comprises a fluoride ion source comprising sodium fluoride.

In an implementation, the oral care composition further comprises silica, water, sodium lauryl sulfate, betaine, sodium carboxy methyl cellulose, saccharin, sorbitol, poly ethylene glycol, tetra sodium pyrophosphate, or combinations thereof.

In an embodiment there is a method of making an oral care composition, comprising: mixing pectin, an anticaries agent and a moisturizing agent to form an orally acceptable vehicle, wherein the pectin comprises an amount of from about 0.1% to about 1% by weight.

In an example, the moisturizing agent comprises coconut oil. In an example, the coconut oil is present in an amount greater than about 0.01% to less than about 5% by weight. In an example, the coconut oil is present in an amount of about 2.5% by weight.

In an example the anticaries agent comprises a fluoride ion source.

In an example the oral care composition exhibits a viscosity greater than about 400,000 centipoise.

In an embodiment, there is a method of treating or preventing dry mouth in the oral cavity, comprising: applying in the oral cavity a composition comprising: pectin in an amount of from about 0.1% to about 1% by weight, an anticaries agent; and a moisturizing agent.

In an example, the moisturizing agent comprises coconut oil. In an example, the coconut oil is present in the composition in an amount greater than about 0.01% to less than about 5% by weight.

Further areas of applicability of the present invention will become apparent from the detailed description provided hereinafter. It should be understood that the detailed description and specific examples, while indicating some preferred aspects of the invention, are intended for purposes of illustration only and are not intended to limit the scope of the invention.

DETAILED DESCRIPTION

The following description of various preferred aspects is merely exemplary in nature and is in no way intended to limit the invention, its application, or uses.

As used throughout, ranges are used as shorthand for describing each and every value that is within the range, including the endpoints. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material as compared to the total weight of the composition.

The oral care compositions of the various embodiments preferably are in the form of a dentifrice. The term "dentifrice" as used throughout this description, denotes a paste, gel, or liquid formulation, for example, a toothpaste. The dentifrice may be in any desired form, such as a paste or a gel, which may be deep striped, surface striped, multi-layered, having the gel surround the paste, or any combinations thereof.

The term "orally acceptable vehicle" as used throughout this description means a vehicle or composition in which any ingredient that is present in the composition is in an amount and form which does not render the composition unsafe, unpalatable, or otherwise unsuitable for use in the oral cavity. An orally acceptable vehicle may be any composition containing any single or combination of the following components: anticaries active agents, viscosity modifiers, moisturizer agents, thickening agents, humectants, pH modifying agents, anticalculus agents, abrasives, surfactants, coloring agents, flavor agents, sweetening agents, water, and mixtures thereof.

In an embodiment, an oral care composition comprises: an orally acceptable vehicle comprising pectin in an amount of from about 0.1% to about 1% by weight, an anticaries agent, and a moisturizing agent. Such an oral care composition may be used for treating or preventing a condition of the oral cavity, for example, by delivering the composition to the oral cavity.

To prepare an oral care composition of the embodiments, an anticaries active agent, a moisturizer agent, and a viscosity modifier comprising pectin in an amount of from about 0.1 wt % to about 1 wt % are incorporated into an orally acceptable vehicle. The moisturizing agent of the embodiments may be coconut oil, such as in an amount in the range of from about 0.1% to about 5% by weight, for example, 2.5% by weight.

In some embodiments, the oral care composition is a paste or gel. In some embodiments, the constituents of the oral care composition are chosen to form a dentifrice composition that may have viscosity of at least about 200,000 centipoise, such as at least 400,000 centipoise, for example at least 500,000 centipoise. In one embodiment, the oral care composition comprises a toothpaste that includes 1.0% pectin and 2.5% coconut oil, by weight, and has a viscosity of at least 500,000 centipoise.

The oral care composition may comprises at least one abrasive. The abrasive agent may be selected from, but is not limited to, the group consisting of silica, alumina, insoluble phosphate, calcium carbonate, resinous abrasive, and mixtures thereof.

The oral care composition further comprises at least one humectant, and at least one surfactant, diluents, pH modifying agents, foam modulators, thickening agents, sweeteners, flavorant, anticalculus or tartar control agents, and mixtures thereof. In an example, the anticaries agent comprises a fluoride ion source. In an example, the anticaries agent comprises a fluoride ion source comprising sodium fluoride.

In an embodiment there is a method of making an oral care composition, comprising: mixing pectin, an anticaries agent and a moisturizing agent to form an orally acceptable vehicle, wherein the pectin comprises an amount of from about 0.1% to about 1% by weight. As described above, the moisturizing agent may comprise coconut oil, for example, in an amount greater than about 0.01% to less than about 5% by weight. In an example, the coconut oil is present in an amount of about 2.5% by weight.

In an embodiment, there is a method of treating or preventing dry mouth in the oral cavity, comprising: applying in the oral cavity a composition comprising: pectin in an amount of from about 0.1% to about 1% by weight, an anticaries agent; and a moisturizing agent. As described above, in an example, the moisturizing agent comprises coconut oil. In an example, the coconut oil is present in the composition in an amount greater than about 0.01% to less than about 5% by weight.

In an embodiment, compositions described herein may be formed by combination of several ingredients. Three phases of the various ingredients may be incorporated in the oral care composition. For example, an aqueous phase, a gel phase and a solid phase. The aqueous phase may contain an anticaries active agent such as fluoride ion source, a sweetener such as saccharin, a colorant and water. The gel phase can contain at least one humectants, a thickening agent, anticalculus agent, and a viscosity modifier such as pectin. The solids phase can be comprised of abrasives, surfactant, flavor, coconut oil, and breath freshening films.

Anticaries Active Agents

In at least one embodiment, the oral care composition includes an anticaries agent. The anticaries agent may be at least one chosen from a fluoride ion source, for example, a fluoride ion providing compound. Exemplary fluoride ion providing compounds include soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al, and U.S. Pat. No. 3,678,154, to Widder et al. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, and sodium monofluorophosphate as well as mixtures thereof.

In certain embodiments, the oral care composition of the present disclosure may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, or e.g., about 1450 ppm. The appropriate level of fluoride will depend on the particular application. A toothpaste for general consumer use would typically have about 1000 to about 1500 ppm, with pediatric toothpaste having somewhat less. A dentifrice for professional application could have as much as about 5,000 or even about 25,000 ppm fluoride. Fluoride ion sources may be incorporated in the compositions disclosed herein at a level of about 0.001% to about 10 wt %, such as about 0.003% to about 5%, for example, or about 0.01% to about 1.0%, by weight. In an embodiment, the anticaries agent comprises sodium fluoride in an amount ranging from greater than 0 wt % to about 0.24% by weight.

Other anticaries agents may include arginine salts such as anginine bicarbonate, arginine phosphate, and arginine bicarbonate.

Moisturizing Agent

In at least one embodiment, the oral care composition includes a moisturizing agent. The moisturizing agents may reduce, or possibly eliminate the drying out of the mucosa of the oral cavity. In some embodiments, the moisturizing agent includes coconut oil, castor oil, avocado oil, flaxseed oil, plant derived glyceride oils, or combinations thereof. In an embodiment, the moisturizer agent comprises coconut oil and is present in an amount of from about 0.1% to about 5%. In an embodiment, the moisturizer agent comprises coconut oil and is present in an amount of about 2.5%. Coconut oil may be procured from commercial sources as partially hydrogenated coconut oil (e.g., Cargill RBD HYD Ultimate 92 Coconut Oil-29390 cas# is 084836-98-6).

Thickening Agent

In at least one embodiment, the oral care composition may include a thickening agent. Exemplary thickening agents, also referred to as "thickeners", for use in the orally acceptable vehicle include organic and inorganic thickeners. For example, an oral care composition of an embodiment may comprise silica thickeners, which form polymeric structures or gels in aqueous media. Silica thickeners such as Zeodent 115 and Zeodent 165 (both available from Huber Engineered Materials) and DT 267 (available from PPG Industries or OSC—Lianji Chemical Industry Co., Ltd.) may be used. Note that these silica thickeners are physically and functionally distinct from particulate silica abrasives, which may also present in the oral care composition, as the silica thickeners are very finely divided and provide little or no abrasive action. Other thickening agents may be selected from starch, polyvinylpyrrolidone, carboxyvinyl polymers, carrageenan (Irish moss), hydroxyethyl cellulose and water soluble salts of cellulose ethers such as carboxymethyl cellulose (CMC) including sodium carboxymethyl cellulose and sodium carboxymethyl hydroxyethyl cellulose. Natural gums such as karaya, gum arable, and gum tragacanth can also be incorporated as additional thickeners. Colloidal magnesium aluminum silicate can also be used as component of the thickening agent's composition to further improve the oral care composition's texture. In certain embodiments, the one or more thickening agent may be incorporated in an oral care composition in an amount of from about 0.5% to about 5% by weight, for example, from about 0.1% to about 1.0%, by weight.

In an embodiment, the thickening agent may further function as a viscosity modifier. Hydrocolloids are examples of thickening agents. Pectin, one hydrocolloid, has the ability to modify viscosity with its ability to gel. Thus, in at least one embodiment, the thickening agent comprises a viscosity modifier comprising pectin. Pectin is a naturally occurring biopolymer comprising of a mixture of polysaccharides from plants, and may be extracted from the cell wall of citrus peels. Pectin may also be purchased. For example, pectin is available from commercial sources as a powder (e.g., from CP Kelco. with a product name GENU® Pectin, cas# 9000-69-5). The pectin may be included in an amount of from about 0.1% to about 2%, such as from about from about 0.2% to about 1.5%, for example, from about 0.5% to about 1.0% by weight of the total oral care composition. In an embodiment, the oral care composition comprises about 1.0% pectin by weight. In an embodiment, the oral care composition comprises about 2.5% coconut oil and about 1% pectin, by weight. Other viscosity modifiers include food grade polysaccharides such as lecithin, for example, in addition to or as an alternative to pectin, carrageenan, guar gum and the like.

Humectant

In at least one embodiment, the oral care composition may include one or more humectants. Humectants prevent the oral care composition from hardening upon exposure to air. Certain humectants can also impart desirable sweetness or flavor to dentifrice compositions. Suitable humectants include edible polyhydric alcohols such as glycerine, sorbitol, xylitol, propylene glycol as well as other polyols and mixtures of these humectants. In certain embodiments, one or more humectant may be incorporated in oral care compositions in an amount of about 10% to about 60% by weight, for example, in an amount of from about 20% to about 65%, for example, from about 25% to about 60%, such as about 30% to about 57% by weight.

pH Modifying Agent

At least one embodiment of an oral care composition may include one or more pH modifying agent. The one or more pH modifying agent can include acidifying agents to lower pH, basifying agents to raise pH, and/or buffering agents to control pH within a desired range. For example, one or more compounds selected from acidifying, basifying and buffering agents can be included to provide a pH of 2 to 10, or in various illustrative embodiments, 2 to 8, 3 to 9, 4 to 8, 5 to 7, 6 to 10, 7 to 9, etc. Any orally acceptable pH modifying agent can be used, including without limitation, carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range. In certain embodiments, one or more pH modifying agent may be incorporated in oral care compositions in an amount of about 0.01% to about 1.5% by weight. In one embodiment of the present disclosure, the pH modifying agent is a buffering agent comprising tetrasodium pyrophosphate, which may be present in an amount of about 0.1% to about 0.5% by weight.

Anticalculus Agent

In at least one embodiment, the oral care composition may include an anticalculus agent. Suitable anticalculus agents include without limitation polyaminopropanesulfonic acid (AMPS), phosphates and polyphosphates (for example pyrophosphate salts), including the mono, di, tri and tetra alkali metal and ammonium pyrophosphate and tripolyphosphate salts, hexametaphosphate salts, zinc citrate trihydrate, polypeptides, polyolefin sulfonates, polyolefin phosphates, and diphosphonates. In some embodiments, the anticalculus agent is present in an amount of about 0.1% to about 0.5% by weight. In some embodiments, the oral care composition comprises a mixture of anticalculus agents. In some embodiments, tetrapotassium pyrophosphate (TKPP), tetrasodium pyrophosphate (TSPP) and sodium tripolyphosphate (STPP) are used as the anticalculus agents.

Abrasive

In at least one embodiment, the oral care composition may include one or more abrasive. The one or more abrasive may include precipitated calcium carbonate (e.g. prepared from reaction of calcium oxide with water and carbon dioxide), natural refined calcium carbonate (e.g., from mineral sources), or mixtures thereof. Natural calcium carbonate may have a somewhat harder, more crystalline structure than precipated calcium carbonate, and in a particular embodiment, the calcium carbonate abrasive is a mixture of the two. The calcium carbonate base portion may also comprise silica abrasives and/or additional abrasives, e.g., a calcium phosphate abrasive, e.g., tricalcium phosphate $(Ca_3(PO_4)_2)$ hydroxyapatite $(Ca_{10}(PO_4)_6(OH)_2)$, or dicalcium phosphate dihydrale $(CaHPO_4 2H_2O)$ or calcium pyrophosphate; or abrasives such as sodium metaphosphate, potassium metaphosphate. aluminum silicate, calcined alumina, bentonite or other siliceous materials, or combinations thereof. The concentration of abrasive in the oral care compositions of the embodiments will normally be in the range of from 5% to 40% by weight, for example, 5% to 30% by weight, such as 10 to 25% by weight, for example, 10% to 20% by weight of the composition. Exemplary abrasives that may be used include silica abrasives such as precipitated or hydrated silicas having a mean particle size of up to about 20 microns, such as Zeodent 105 and Zeodent 114, and Zeodent 165 marketed by J. M. Huber Chemicals Division, Havre de Grace, Md. 21078, or Sylodent 783 marketed by Davison Chemical Division of W. R. Grace & Company. Abrasives such as Sorbosil AC 43 from PQ Corporation may also be included. Other useful dentifrice abrasives include aluminium oxide, aluminum silicate, calcined alumina, bentonite or other siliceous materials, insoluble phosphates, and mixtures thereof.

Surfactant

In at least one embodiment, the oral care composition may include one or more surfactant. The surfactant is preferably anionic or nonionic in nature. Surfactants may be included, if desired. Examples of suitable surfactants include water-soluble salts of higher fatty acid monoglyceride monosulfates, such as the salt of monosulfated monoglyceride of hydrogenated coconut oil fatty acids; higher alkyl sulfates such as sodium lauryl sulfate (SLS); alkyl aryl sulfonates such as sodium dodecyl benzene sulfonate; higher alkyl sulfoacetates, such as sodium lauryl sulfoacetate; higher fatty acid esters of 1,2-dihydroxypropane sulfonate; and the substantially saturated higher aliphatic acyl amides of lower aliphatic amino carboxylic compounds, such as those having 12-16 carbons in the fatty acid, alkyl or acyl radicals; and the like. Examples of the last mentioned amides include N-lauryl sarcosine, and the sodium, potassium and ethanolamine salts of N-lauryl, N-myristoyl, or N-palmitoylsarcosine. Others include, for example, nonanionic polyoxyethylene surfactants, such as Polyoxamer 407, Steareth 30, Polysorbate 20, and castor oil; and amphoteric surfactants, such as cocamidopropyl betaine (tegobaine), and cocamidopropyl betaine lauryl glucoside; condensation products of ethylene oxide with various hydrogen containing compounds that are reactive therewith and have long hydrocarbon chains (e.g., aliphatic chains of from 12 to 20 carbon atoms), which condensation products (ethoxamers) contain hydrophilic polyoxyethylene moieties, such as condensation products of poly(ethylene oxide) (also known as polyethylene glycol, or PEG) with fatty acids, fatty, alcohols, fatty amides and other fatty moieties, and with propylene oxide and polypropylene oxides. In an example, surfactants may be derived from coconut oil or other vegetable oils by, for example, saponification (i.e., reacting fatty acids with hydroxide or sulfuric acid) as is understood in the art.

Flavoring Agent(s):

In at least one embodiment, the oral care composition of the present disclosure may include one or more flavoring agent. Flavoring agents which are used in various embodiments include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.3 to about 5% by weight e.g. about 0.5 to about 1.5% by weight. In an embodiment, the flavoring agent may be incorporated in the oral composition at a concentration of about 0.1% to about 2.0% by weight.

Sweeteners

In at least one embodiment, the oral care composition may include one or more sweetener. Sweeteners may include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof such as sodium saccharin, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.01% to about 3.0%, optionally from about 0.1% to about 0.3. In one embodiment, one or more sweeteners in an amount of 0.1% to 1.0% may be used.

Coloring Agents

In at least one embodiment, the oral care composition may include one or more colorant. The one or more colorant may be at least one pigment and/or at least one dye. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5-1000 microns, preferably 250-500 microns, and are present at a concentration of from about 0.01% to about 5%, such as from about 0.1% to about 3.0 by weight.

Dyes used are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphto-6-monosulfonate), FD&C Green No. 3 (disodium slat of 4-{[4-(N-ethyl-p-sulfobenzyno)-phenyl]-(4-hydroxy-2-sulfoniumphen-yl)mewthylene}-[1-(N-ethyl-N-p-sulfobenzyl)-G)-3, 5cyclohexadienimine], FD&C Blue No. 1 (disodium salt of dibenzyldiethyldiaminotriphenylcarbinol trisulfonic acid of indigo tin) and mixtures thereof in various proportions. In various embodiments, the concentration of the dye in the oral care composition is in an amount of from about 0.0001% to about 3%, such as from about 0.001% to about 1%, for example, from about 0.0015% to about 0.5% by weight.

Aqueous Carrier

In at least one embodiment, the oral care composition may be an aqueous composition that includes a water phase. In an example, the aqueous composition may comprise a separate water phase or aqueous solution in combination with a gel or paste phase. In an example, the oral care composition may include water in an amount of from about 1% to about 30%, such as from about 5% to about 20%, for example, from about 5% to about 15% by weight.

Additional ingredients known by those skilled in the art for use in oral care may be included in the oral care composition.

Methods

In some embodiments, the present disclosure provides methods to clean an oral surface and ameliorate dry mouth in a human or animal subject using a high viscosity composition. The method may include applying an oral care composition as described the present disclosure to a toothbrush and contacting a tooth surface and other oral cavity surfaces with the oral care composition. As used herein "animal subject" includes non-human mammals, such as canines, felines and horses. In one embodiment, the oral care composition is viscous to a degree that prevents sinking of the oral care composition between the bristles of a toothbrush, and the viscous oral care composition is contacted with an oral surface of the mammalian subject to thereby clean teeth and to provide relief from the symptoms of dry mouth.

In various embodiments, the oral care composition prepared in accordance with the present disclosure may be applied regularly to an oral surface, for example on a daily basis, at least one time daily for multiple days, or alternately every second or third day. In some embodiments, the oral care composition is applied to the oral surfaces from 1 to 3 times daily, for at least 2 weeks up to 8 weeks, from four months to three years, or more up to a lifetime.

In some embodiments, the oral care composition may be embodied as a gel or a paste and may be applied to the teeth using a toothbrush.

In some embodiments, application of the oral care composition to a surface(s) in the oral cavity provides a clean yet moist feel in the oral cavity. In some embodiments, application of the oral care composition to an oral cavity results in positive mouth and/or tooth feel. In some embodiments, positive mouth and/or tooth feel includes at least one of the following qualities: superior clean feeling, fresh feeling, shiny tooth appearance, smooth tooth feel, cool mouth feel, fresh breath, moist mouth, hydrated mouth and extended or lasting fresh breath.

In some embodiments, the oral care composition is a dentifrice composition. In some embodiments the dentifrice composition is a toothpaste and/or gel. In some embodiments, the oral care composition is applied directly to the teeth, such as by a toothbrush, by hand, by swab or by a film or strip.

EXAMPLES

Example 1

Preparation of Toothpaste Compositions

Various toothpaste compositions according to at least one embodiment described herein were prepared by combining the ingredients listed in and in the amounts set forth in Table 1 below. The resulting oral care compositions were observed to have an enhanced product appearance.

For example, water, sweetener, fluoride and colorant were mixed to form an aqueous phase. A gel phase was formed by dispersing a thickening agent and pH modifier and a humectant in polyethylene glycol (PEG). The gel phase was then mixed with the aqueous phase to form a mixture. Abrasive silica was then added to the mixture and mixed until wet. Coconut oil was then added and mixed in for about 20 to 30 minutes under vacuum. Flavorant was then added and mixed for about 2-3 minutes followed by addition of sodium lauryl sulfate (SLS) and amphoteric surfactant with mixing for 3 to 5 minutes resulting in a composition according to Table 1.

TABLE 1

| Ingredient | Weight % Range |
| --- | --- |
| Water, flavor, colorant and sweetener | 10-15 |
| Coconut Oil | 0.1-5 |
| Pectin | 0.1-1 |
| Amphoteric surfactant | 0.5-3 |

TABLE 1-continued

| Ingredient | Weight % Range |
| --- | --- |
| Sodium Lauryl Sulfate | 0.5-3 |
| pH modifier | 0.1-0.75 |
| Sodium Fluoride | 0.1-0.5 |
| Humectant | 45-60 |
| Polyethylene Glycol | 1-5 |
| Thickening agent | 1-5 |
| Abrasive Silica | 5-15 |
| White Film (canola free) | 0.1-1 |
| High Cleaning Silica (optional) | 5-15 |

Example 2

Viscosity Measurements

Four toothpaste compositions were prepared according to the method described in Example 1 but with each composition comprising 2.5% coconut oil, and varying only in their respective amounts of pectin (0%, 0.25%, 0.5%, and 1.0%, by weight). The viscosities of all four of the toothpaste compositions were measured by Brookfield viscometer at speed 1rpm using the V74 spindle flow method and the exhibited results are shown in Table 2.

TABLE 2

| Toothpaste Composition | Amount of Coconut Oil (wt %) | Amount of Pectin (wt %) | Viscosity (cP) |
| --- | --- | --- | --- |
| Comparative | 2.5 | 0 | 319000.0 |
| A | 2.5 | 0.25 | 284200.0 |
| B | 2.5 | 0.5 | 290000.0 |
| C | 2.5 | 1.0 | 562600.00 |

The addition of pectin in composition A and B surprisingly had only a minor effect on viscosity as compared to the comparative composition. The addition of pectin in composition C, however, resulted in a non-linear increase in viscosity as compared to compositions A and B and exhibited an unexpectedly higher viscosity than that measured for the comparative composition.

While not limited to any particular theory, it is believed that the unexpected increase in viscosity by increasing the amount of pectin from 0.5% by weight as in Composition B to 1.0% by weight as in Composition C can be attributed to the fact that pectin is a hydrocolloid that is used not only as a thickening agent, but also as a gelling agent. Gel formation is the phenomenon involving the association or cross-linking of the polymer chains to form a three dimensional network. The viscosity generally changes with concentration, temperature, and shear strain rate in a complex manner dependent on the hydrocolloid, and other material present. Surprisingly the viscosity of the formulation increased in a non-linear manner when pectin concentration was increased to 1.0% in comparison to 0.25-0.5% in the invention formula.

Example 3

Toothbrush Bristle Penetration

Two toothpaste compositions were prepared according to the method described in Example 1, with each composition comprising 2.5% coconut oil and only one of the compositions comprising pectin (1.0%) (i.e., Comparative Composition and Composition C). A nurdle of Comparative toothpaste composition was dispensed onto the bristles of a first flat trimmed toothbrush ("toothbrush 1") and a nurdle of toothpaste composition C was dispensed onto the bristles of a second flat-trimmed toothbrush ("toothbrush 2"). Toothbrushes 1 and 2 were observed as being nearly identical. Upon inspection it was observed that the nurdle of the comparative toothpaste composition appeared less rigid in its form and sank more into the bristles of toothbrush 1 than did the nurdle of toothpaste composition C into the bristles of toothbrush 2.

Toothbrush 1 with the nurdle of comparative toothpaste composition and toothbrush 2 with the nurdle of toothpaste composition C were weighed separately. A spatula was then used to remove each of the nurdles by sliding it across the top surface of the bristles of each toothbrush. Each toothbrush was weighed again after removal of the nurdles of toothpaste. The amount of toothpaste removed was calculated based on the difference in weight before/after removal of the toothpaste with the results shown in Table 3 below.

TABLE 3

| Toothbrush | Toothpaste Composition | Amount of Coconut Oil (wt %) | Amount of Pectin (wt %) | % Toothpaste Removed | Std. Dev |
|---|---|---|---|---|---|
| 1 | Comparative | 2.5 | 0 | 86.5 | 2.18 |
| 2 | C | 2.5 | 1.0 | 95.6 | 0.261 |

As shown in Table 3, a larger relative amount of toothpaste composition C was calculated as having been removed from toothbrush 2 as compared to the relative amount of the comparative toothpaste composition that was removed from toothbrush 1. Visual inspection of each toothbrush was performed. More of the comparative toothpaste composition was observed as having been left behind on and in-between the bristles of toothbrush 1 than that of toothpaste composition C left behind on and in-between the bristles of toothbrush 2. It was determined that composition C had an enhanced product appearance as compared to the comparative toothpaste composition.

What is claimed is:

1. An oral care composition, comprising:
an orally acceptable vehicle comprising
pectin in an amount of about 1% by weight,
an anticaries agent;
a humectant in an amount of from 45% to 60% by weight;
a thickening agent which is not pectin in an amount of from 1% to 5% by weight;
water in an amount of from 5% to 15% by weight; and
a moisturizing agent,
wherein the moisturizing agent comprises coconut oil, wherein the coconut oil is present in an amount of about 2.5% by wt. from 0.1% to 5% by weight, wherein the composition exhibits a viscosity greater than about 500,000 centipoise, and wherein the composition is a toothpaste or gel.

2. The oral care composition of claim 1, further comprising at least one abrasive.

3. The oral care composition of claim 2, wherein the abrasive agent is selected from the group consisting of silica, alumina, insoluble phosphate, calcium carbonate, resinous abrasive, and mixtures thereof.

4. The oral care composition of claim 1, further comprising at least one surfactant.

5. The oral care composition of claim 1, further comprising one or more agents selected from abrasives, diluents, pH modifying agents, surfactants, foam modulators, sweeteners, flavorant, anticalculus or tartar control agents, and mixtures thereof.

6. The oral oral care composition of claim 1, further comprising silica, water, sodium lauryl sulfate, betaine, sodium carboxy methyl cellulose, saccharin, poly ethylene glycol, tetra sodium pyro phosphate, or combinations thereof.

7. The oral care composition of claim 1, wherein the anticaries agent comprises a fluoride ion source.

8. The oral care composition of claim 1, wherein the anticaries agent comprises a fluoride ion source comprising sodium fluoride.

9. A method of making an oral care composition, comprising:
mixing pectin, an anticaries agent and a moisturizing agent to form an orally acceptable vehicle,
wherein the pectin comprises an amount of about 1% by weight, wherein the moisturizing agent comprises coconut oil, wherein the coconut oil is present in an amount of about 2.5% from 0.1% to 5% by weight, wherein the composition comprises a humectant in an amount of from 45% to 60% by weight, a thickening agent which is not pectin in an amount of from 1% to 5% by weight, and water in an amount of from 5% to 15% by weight, wherein the composition exhibits a viscosity greater than about 500,000 centipoise, and wherein the composition is a toothpaste or gel.

* * * * *